United States Patent
Jenison et al.

(10) Patent No.: US 10,653,887 B2
(45) Date of Patent: May 19, 2020

(54) METHODS, IMPLANTABLE MEDICAL DEVICES, AND SYSTEMS TO CONTINUE IMPLEMENTING A SPECIAL MODE OF OPERATION AFTER EXPERIENCING A DEVICE RESET

(71) Applicant: Medtronic, Inc., Minneapolis, MN (US)

(72) Inventors: Troy A. Jenison, Roseville, MN (US); Michael D. Levy, Maple Grove, MN (US); Benjamin P. Rhodes, Columbia Heights, MN (US); Christopher C. Stancer, Prescott, WI (US)

(73) Assignee: Medtronic, Inc., Minneapolis, MN (US)

( * ) Notice: Subject to any disclaimer, the term of this patent is extended or adjusted under 35 U.S.C. 154(b) by 181 days.

(21) Appl. No.: 15/662,531

(22) Filed: Jul. 28, 2017

(65) Prior Publication Data

US 2017/0319857 A1 Nov. 9, 2017

Related U.S. Application Data

(62) Division of application No. 14/168,938, filed on Jan. 30, 2014, now Pat. No. 9,724,520.

(51) Int. Cl.
*A61N 1/37* (2006.01)
*A61N 1/372* (2006.01)
(Continued)

(52) U.S. Cl.
CPC ....... *A61N 1/3718* (2013.01); *A61M 5/14276* (2013.01); *A61N 1/08* (2013.01);
(Continued)

(58) Field of Classification Search
CPC ...... A61N 1/3718; A61N 1/08; A61N 1/3925; A61N 1/37235; A61N 1/36142;
(Continued)

(56) References Cited

U.S. PATENT DOCUMENTS 5,464,435 A * 11/1995 Neumann .......... A61N 1/36514
607/9
5,647,379 A 7/1997 Meltzer
(Continued)

FOREIGN PATENT DOCUMENTS

| EP | 0753327 A2 | 1/1997 |
| WO | 2010031033 A1 | 3/2010 |
| WO | 2011049639 A1 | 4/2011 |

OTHER PUBLICATIONS

Barr, Michael. "Memory Types," Embedded Systems Programming, May 2001, pp. 103-104, https://barrgroup.com/Embedded-Systems/How-To/Memory-Types-RAM-ROM-Flash, viewed on Mar. 18, 2018.*

(Continued)

*Primary Examiner* — Carl H Layno
*Assistant Examiner* — James Moss

(57) ABSTRACT

An implantable medical device implements a special mode of operation, such as a mode of electrical stimulation therapy, during conditions where there may be an increased likelihood that a device reset will occur. The implantable medical device recovers from the device reset by copying values that specify the special mode and that are stored in a non-volatile memory to an operating memory. The special mode is implemented after the device reset has occurred by using the values copied to the operating memory. One version of the special mode is an MRI mode that allows the implantable medical device to safely operate during an MRI scan. The fields of the MRI scan may trigger a device reset, but the MRI mode values are copied from the non-volatile (Continued)

memory to the operating memory, and the MRI mode is implemented after the reset by using the values copied to the operating memory.

13 Claims, 7 Drawing Sheets

(51) Int. Cl.
- *A61N 1/39* (2006.01)
- *A61N 1/08* (2006.01)
- *A61M 5/142* (2006.01)
- *A61N 1/36* (2006.01)

(52) U.S. Cl.
CPC ....... *A61N 1/37235* (2013.01); *A61N 1/3925* (2013.01); *A61M 2205/50* (2013.01); *A61M 2210/0693* (2013.01); *A61M 2210/1003* (2013.01); *A61N 1/36142* (2013.01)

(58) Field of Classification Search
CPC ...... A61M 5/14276; A61M 2210/0693; A61M 2205/50; A61M 2210/1003
USPC .......................................................... 607/3
See application file for complete search history.

(56) References Cited

U.S. PATENT DOCUMENTS

| | | |
|---|---|---|
| 6,188,926 B1 | 2/2001 | Vock |
| 6,678,560 B1 | 1/2004 | Gilkerson et al. |
| 6,937,906 B2 | 8/2005 | Terry et al. |
| 6,963,779 B1 | 11/2005 | Shankar |
| 7,050,855 B2 | 5/2006 | Zeijlemaker et al. |
| 7,076,283 B2 | 7/2006 | Cho et al. |
| 7,082,328 B2 | 7/2006 | Funke |
| 7,212,863 B2 | 5/2007 | Strandberg |
| 7,363,080 B2 | 4/2008 | Stubbs et al. |
| 7,369,898 B1 | 5/2008 | Kroll et al. |
| 7,373,200 B2 | 5/2008 | Stubbs et al. |
| 7,483,744 B2 | 1/2009 | Stubbs et al. |
| 7,672,726 B2 | 3/2010 | Ginggen |
| 7,693,568 B2 | 4/2010 | Zeijlemaker |
| 7,729,770 B2 | 6/2010 | Cabelka et al. |
| 7,917,212 B2 | 3/2011 | Yonce et al. |
| 8,014,867 B2 | 9/2011 | Cooke et al. |
| 8,121,678 B2 | 2/2012 | Linder et al. |
| 8,260,422 B2 | 9/2012 | Ellingson et al. |
| 9,320,883 B2 | 4/2016 | Huelskamp et al. |
| 2001/0041920 A1 | 11/2001 | Starkweather et al. |
| 2003/0144706 A1 | 7/2003 | Funke |
| 2004/0030323 A1* | 2/2004 | Ullestad ............ A61M 5/14276 604/891.1 |
| 2005/0070786 A1 | 3/2005 | Zeijlemaker et al. |
| 2005/0070975 A1 | 3/2005 | Zeijlemaker et al. |
| 2006/0167496 A1 | 7/2006 | Nelson et al. |
| 2006/0173295 A1 | 8/2006 | Zeijlemaker |
| 2006/0293591 A1 | 12/2006 | Wahlstrand et al. |
| 2007/0021785 A1 | 1/2007 | Inman et al. |
| 2007/0021814 A1 | 1/2007 | Inman et al. |
| 2007/0091687 A1* | 4/2007 | Armstrong ......... A61N 1/37264 365/185.29 |
| 2007/0173890 A1 | 7/2007 | Armstrong |
| 2007/0173910 A1 | 7/2007 | Armstrong |
| 2007/0265685 A1 | 11/2007 | Zeijlemaker |
| 2009/0138058 A1 | 5/2009 | Cooke et al. |
| 2009/0326595 A1* | 12/2009 | Brockway ............ A61B 5/0031 607/3 |
| 2010/0211123 A1 | 8/2010 | Stubbs et al. |
| 2011/0077706 A1 | 3/2011 | Ellingson et al. |
| 2011/0093046 A1 | 4/2011 | Ellingson et al. |
| 2011/0106204 A1 | 5/2011 | Yoon et al. |
| 2011/0106218 A1 | 5/2011 | Stancer et al. |
| 2011/0160786 A1* | 6/2011 | Stubbs ..................... A61N 1/37 607/14 |
| 2011/0160791 A1 | 6/2011 | Ellingson et al. |
| 2011/0196449 A1 | 8/2011 | Jenison |
| 2011/0202104 A1 | 8/2011 | Butala |
| 2011/0208268 A1 | 8/2011 | Brown |
| 2011/0238135 A1 | 9/2011 | Marnfeldt et al. |
| 2011/0257798 A1* | 10/2011 | Ali .................... A61M 5/16831 700/282 |
| 2012/0010676 A1 | 1/2012 | Zeijlemaker |

OTHER PUBLICATIONS

David Patterson et al., "Computer Organization and Design: The Hardware/Software Interface", Third Edition the Morgan Kaufmann Series in Computer Architecture and Design, Elsevier, Aug. 7, 2004, https://books.google.com/books?id=1lD9LZRclZ8C&pg=PA23&lpg=PA23&hl=en#v=onepage&q&f=false, viewed on Mar. 18, 2019.*

Jeff Tyson "How Computer Memory Works" Aug. 23, 2000. HowStuffWorks.com. <https://computer.howstuffworks.com/computer-memory.htm> Mar. 19, 2019.*

Deepanshi Mittal, "Types of computer memory (RAM and ROM)", https://www.geeksforgeeks.org/types-computer-memory-ram-rom/, viewed on Mar. 20, 2019.*

(PCT/US2015/012150) PCT Notification of Transmittal of the International Search Report and the Written Opinion of the International Searching Authority, dated Apr. 17, 2015, 10 pages.

Jenison et al., "Methods, Implantable Medical Devices, and Systems to Continue Implementing a Special Mode of Operation After Experiencing a Device Reset", Notice on First Office Action for Chinese Patent Application No. 201580017206.8, dated Apr. 3, 2018, 6 pages.

* cited by examiner

METHODS, IMPLANTABLE MEDICAL DEVICES, AND SYSTEMS TO CONTINUE IMPLEMENTING A SPECIAL MODE OF OPERATION AFTER EXPERIENCING A DEVICE RESET

RELATED APPLICATIONS

This application is a divisional of U.S. patent application Ser. No. 14/168,938, filed Jan. 30, 2014 (now allowed and granting as U.S. Pat. No. 9,724,520), the content of which is incorporated by reference herein its entirety.

TECHNICAL FIELD

Embodiments relate to implantable medical devices that implement a special mode of stimulation while in the presence of a condition that may increase the likelihood of triggering a device reset. More particularly, embodiments relate to implantable medical devices that recover from a device reset by continuing to implement the special mode.

BACKGROUND

Implantable medical devices that provide therapy such as electrical stimulation or drug delivery, are programmed to utilize a special mode just prior to the patient having the implantable medical device undergoing a particular procedure such as a magnetic resonance imaging (MRI) scan. In the case of an MRI, the special mode, referred to herein as an MRI mode, for an implantable medical device that provides stimulation therapy may alter the normal stimulation by utilizing an asynchronous form of pacing that avoids triggering or inhibiting pacing as a function of sensing. The MRI mode avoids the various fields of the MRI machine, including static and time varying magnetic fields as well as radio frequency electromagnetic waves, from causing false sensing of intrinsic signals like intrinsic heartbeats which can lead to improper pacing. As another example, MRI mode in a drug delivery device may better protect the on-board supplies. Furthermore, MRI mode may disconnect a telemetry antenna for some implantable medical devices.

One issue in particular may occur during an MRI scan while the implantable medical device operates in the MRI mode. The fields of the MRI scan may trigger the implantable medical device to experience a device reset, also known as a power on reset. The device reset may impact the operation of the implantable medical device to varying degrees depending upon the severity of the reset. In some cases, the reset may not impact the continued operation of the implantable medical device in the MRI mode because the volatile memory where the programming is stored is not erased. However, in cases where the device reset does erase the programming from the volatile memory, the implantable medical device defaults to a non-MRI mode which is intended for device recovery in non-MRI contexts. This non-MRI mode that is recovered is typically less optimized for operation in the MRI context. This is especially true for implantable cardiac defibrillators that often recover in a non-MRI mode that does not perform pacing and has tachyarrhythmia detection and therapies enabled. As a result, the patient and/or the implantable medical device may be at a greater risk after the device reset.

SUMMARY

Embodiments address issues such as these and others by providing an implantable medical device that stores programming related to a special mode of operation, such as an MRI mode, in non-volatile memory. The special mode is implemented from an operating memory that may be volatile, but if a device reset erases or otherwise corrupts the programming from the operating memory, the implantable medical device recovers by loading the special mode programming from the non-volatile memory to the operating memory. The implantable medical device then continues operating in the special mode.

Embodiments provide a method of operating an implantable medical device during a condition that may trigger a device reset. The method involves receiving mode programming at the device that defines a special mode of operation to utilize during the condition and receiving parameter programming that specifies therapy parameters to utilize for the special mode of operation. The method further involves storing the mode programming and the parameter programming in a non-volatile memory and storing a value in the non-volatile memory indicating whether the special mode is active. Upon experiencing a device reset, the method further involves reading the value that indicates whether the special mode is active and loading the mode programming and parameter programming from the non-volatile memory to an operating memory. In response to reading the value when the value indicates that the special mode is active, the method involves implementing the special mode defined by the mode programming from the operating memory.

Embodiments provide an implantable medical device that operates during a condition that may cause a device reset. The implantable medical device includes a therapy circuit that provides a medical therapy, an operating memory, a non-volatile memory, and a telemetry communication circuit. The implantable medical device further includes a processing device in communication with the therapy circuit, the operating memory, the non-volatile memory, and the telemetry communication circuit. The processing device is configured to receive mode programming at the device that defines a special mode of operation to utilize during the condition and receiving parameter programming that specifies therapy parameters to utilize for the special mode of operation. The processing device is further configured to store the mode programming and the parameter programming in a non-volatile memory and store a value in the non-volatile memory indicating whether the special mode is active. Upon experiencing a device reset, the processing device reads the value that indicates whether the special mode is active, and the processing device loads the mode programming and parameter programming from the non-volatile memory to an operating memory. In response to reading the value when the value indicates that the special mode is active, the processing device implements the special mode defined by the mode programming from the operating memory by controlling operation of the therapy circuit.

Embodiments provide an implantable medical system that operates during a condition that may cause a device reset. The implantable medical device includes an implantable medical lead having a proximal contact and a distal electrode and an implantable medical device. The implantable medical device includes a pulse generator, an electrical connector that is electrically coupled to the pulse generator, the proximal contact being electrically coupled to the electrical connector, an operating memory, a non-volatile memory, and a telemetry communication circuit. The implantable medical device further includes a processing device in communication with the pulse generator, the operating memory, the non-volatile memory, and the telemetry communication circuit. The processing device is configured as discussed above in relation to the implantable medical device embodiments.

Embodiments provide a method of operating an implantable medical device during a condition that may cause a device reset. The method involves receiving programming at the device that relates to a special mode of operation to utilize during the condition and storing the programming in a non-volatile memory. The method further involves storing a value in the non-volatile memory indicating whether the special mode is active and upon experiencing a device reset that terminates a mode of operation occurring prior to the device reset, reading the value that indicates whether the special mode is active and loading the programming from the non-volatile memory to an operating memory. Additionally, in response to reading the value when the value indicates that the special mode is active, the method involves implementing the special mode from the operating memory prior to implementing any other stimulation mode once the device reset has occurred.

Embodiments provide a method of operating an implantable medical device during a condition that may trigger a device reset. The method involves receiving programming at the device that relates to a special mode of operation to utilize during the condition. The method further involves storing the programming in a non-volatile memory and storing a value in the non-volatile memory indicating whether the special mode is active. The method also involves implementing the special mode from the operating memory prior to a device reset and upon experiencing the device reset, detecting prior to loading the mode programming whether the operating memory contains programming of a mode. When it is detected that the operating memory does not contain the programming of the mode then reading the value from the non-volatile memory that indicates whether the special mode is active and when the value indicates that the special mode is active, the method involves loading the programming from the non-volatile memory to an operating memory and implementing the special mode from the operating memory. When it is detected that the operating memory does contain the programming of the mode, then the method involves not loading the programming from the non-volatile memory Embodiments provide a method of operating an implantable medical device during a condition that may trigger a device reset. The method involves receiving programming in an operating memory at the device that relates to a special mode of operation to utilize during the condition. The programming includes a value that indicates whether the special mode is active and the method further involves copying the programming from the operating memory to a non-volatile memory and implementing the special mode from the operating memory prior to a device reset when the value indicates that the special mode is active. Upon experiencing the device reset, the method involves reading the value that indicates whether the special mode is active. Additionally, the method involves copying the programming from the non-volatile memory to the operating memory and when the value indicates that the special mode is active, implementing the special mode from the programming in the operating memory. Upon termination of the special mode, the method involves changing the value in the operating memory that indicates whether the special mode is active to indicate that the special mode is not active and after changing the value, copying the programming that includes the value from the operating memory to the non-volatile memory.

DETAILED DESCRIPTION

Embodiments provide implantable medical systems, devices, and related methods to allow recovery from a device reset while a situation requiring a special mode of operation is present. For instance, embodiments allow for a recovery of a special mode of operation while an implantable medical device (IMD) is in the presence of a condition that may trigger device resets. Information related to the special mode of operation is stored in a non-volatile memory. Upon a device reset occurring while the IMD is operating in the special mode, the information related to the special mode of operation may be copied from the non-volatile memory to an operating memory. The information is then accessed by a processing device from the operating memory to implement the special mode.

Figure 1:
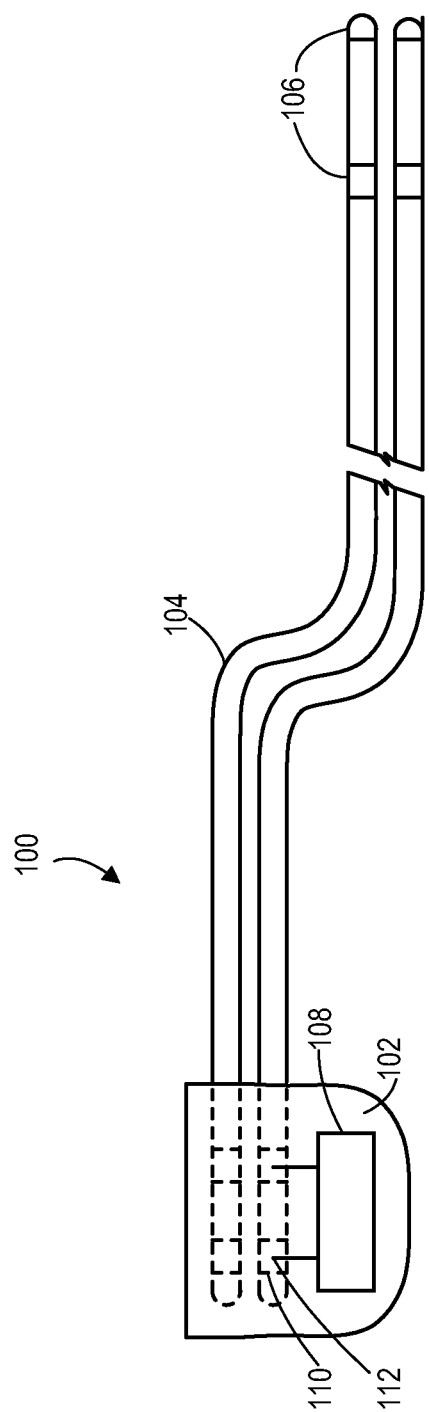
FIG. 1 shows an example of an implantable medical system that implements embodiments to recover from a device reset.

FIG. 1 shows an implantable medical system 100 that may implement a special mode of stimulation when in the presence of a condition that may cause a device reset such as being in close proximity to an MRI machine, a CT machine, a cautery machine, and the like. The implantable medical system 100 may recover from a device reset that occurs while in the special mode by loading special mode values from a non-volatile memory in order to continue providing stimulation therapy in the special mode. Implantable medical system 100 may, for example, represent a pacemaker system, defibrillator system, cardioverter-defibrillator system, cardiac resynchronization system, cardiac loop recorder, or other implantable cardiac system that provides a combination of such therapies or other therapies. Alternatively, implantable medical system 100 may be a non-cardiac system, such as a neurostimulator that may deliver therapy (e.g., electrical signals or drugs) to a spinal cord, brain, pelvic floor or the like, to alleviate pain or treat symptoms of any of a number of neurological or other diseases, or other drug delivery system, such as a diabetes insulin pump.

The remainder of the description refers to the implantable medical system as including an implantable medical device that performs electrical stimulation as the form of medical therapy. However, it is to be appreciated that the details of utilizing the non-volatile memory to recover a special mode of operation when a device reset occurs also applies to other implantable medical devices such as drug pumps that also implement a special mode of operation and therapy parameters configured for the special mode of operation when necessary.

The remainder of the description also refers to an MRI mode as the special mode, where the context is the implantable medical system 100 being in close proximity to an MRI machine. However, it is to be appreciated that the same description also applies to other special modes that may be implemented whenever the implantable medical system 100 is positioned in the presence of a condition that may trigger device resets.

The implantable medical system 100 of this example includes an implantable medical device 102 that includes circuitry 108 that produces stimulation signals. The circuitry 108 is electrically coupled to electrical connectors 112 of the device 102 that create an electrical connection to proximal contacts 110 on a proximal end of an implantable medical lead 104. The lead 104 includes conductors that carry electrical signals to electrodes 106 located on the distal end of the lead 104. The electrodes 106 interface with the tissue of the body to deliver the electrical signals into the tissue at a target site such as within a particular chamber of the heart.

Figure 2:
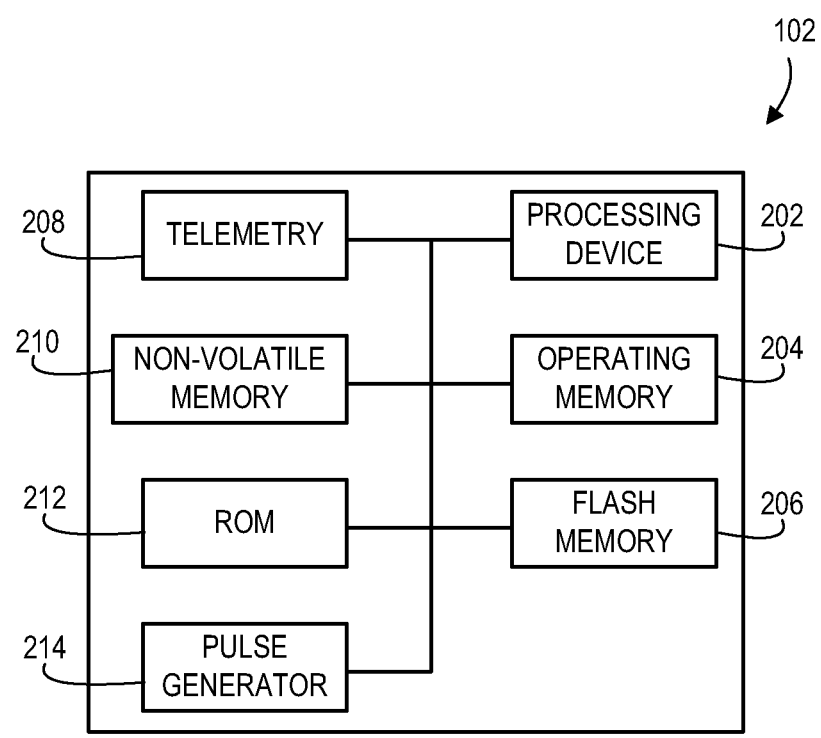
FIG. 2 shows an example of a collection of components of an implantable medical device of the system.

The implantable medical device 102 includes various components within the circuitry 108. An example of these components is shown in FIG. 2. The device 102 includes a processing device 202 such as a general purpose field programmable processor, an application specific field programmable processor, or other type of processing unit that can be programmed and re-programmed while the IMD 102 is implanted. The processing device 202 communicates with other components over one or more data buses.

The processing device 202 communicates with an operating memory 204 that may be a volatile form of memory such as a random access memory (RAM) in order to perform various programmable functions. The processing device 202 may rely on the operating memory 204 to provide the programming values for the operating mode, specifically for the stimulation mode for an IMD 102 that provides electrical stimulation, and the mode parameters to the processing device 202 when the processing device 202 attempts to implement the stimulation therapy. The processor 202 implements the stimulation therapy by controlling the operation of a pulse generator circuit 214 that outputs stimulation pulses to the electrical connector 112 of FIG. 1.

The processing device 202 in this example communicates with other forms of memory as well, including a flash memory 206 which may be programmed with default values for stimulation therapy mode and mode parameters. If the programmable values stored in the operating memory 204 are lost or otherwise corrupted, the processing device 202 may use the default values from the flash 206 in order to continue operation until the programmable values can be reprogrammed into the operating memory 204 at a later time.

The processing device 202 in this example communicates with a read only memory (ROM) 212 in order to bootup and begin basic operations for input/output and for communicating with the various other memory components. Upon the processing device 202 implementing stimulation therapy from the operating memory 204, should both the operating memory 204 and the flash memory 206 become corrupted, the processing device 202 may rely on default values in the ROM 212 to continue the most basic operations such as providing an explant alert communication to an external programming device via a telemetry circuit 208.

The processor 202 may utilize the telemetry circuit 208 for communication with the external programming device for other purposes including receiving initial programmable values that are stored into the operating memory 204 where they can be accessed by the processor 202 for implementation. The telemetry circuit 208 may be of various forms such as a near field communication circuit, a far field communication circuit that utilizes a MICS band, or a combination of the two.

One situation in particular where the telemetry 208 is used by the processor 202 occurs when the IMD 102 will be positioned in the presence of an MRI machine. An external programming device communicates with the IMD 102 through the telemetry circuit 208 in order to set an MRI mode state value to active and to program MRI mode values and MRI mode parameter value into the operating memory 204. This places the IMD 102 into the MRI mode where the IMD 102 provides a different mode of stimulation therapy than when a normal (i.e., non-MRI) mode of stimulation is active. In some embodiments, the IMD 102 may enter MRI mode in other ways, such as by including a magnetic field detector that detects the magnetic field of the MRI machine and provides a signal to the processor 202 which causes the processor 202 to implement the MRI mode which may already be programmed into the operating memory 202 and/or the non-volatile memory 210.

The external programmer may communicate with the IMD 102 through the telemetry circuit 208 to set the MRI mode state to inactive when appropriate or the MRI mode state may be set to inactive in other ways including expiration of a set amount of time.

The IMD 102 also includes a non-volatile memory 210 which may be of various forms including electronically erasable-programmable read only memory (EEPROM), Magnetoresistive random access memory (M-RAM), and ferroelectric random access memory (F-RAM), and the like. The processing device 202 utilizes the non-volatile memory 210 in order to recover the state of the MRI mode, the values for the MRI mode, and the parameter values to be used with the MRI mode when recovering from a device reset.

While the example of the IMD 102 has been described as having several different memory components including the operating memory 204, the Flash 206, the non-volatile memory 210, and the ROM 212, it will be appreciated that other configurations are also applicable. For instance, fewer components may be applicable where all defaults are present in a ROM and the Flash is eliminated. As another example, some of these components may be combined into a single memory component rather than existing separately.

Figure 3:
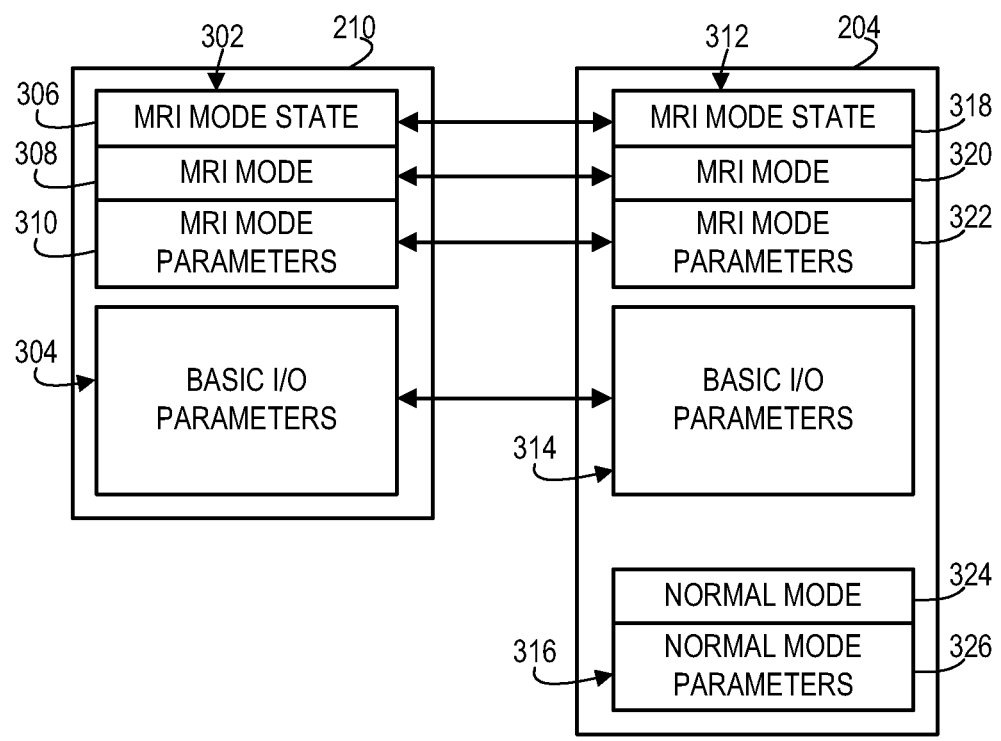
FIG. 3 shows an example of a non-volatile memory and an operating memory of the implantable medical device.

FIG. 3 illustrates the relationship between the non-volatile memory 210 and the operating memory 204. The operating memory 204 and the non-volatile memory 210 may maintain various tables of information. In the operating memory 204, the processor 202 may store a table 314 of basic input/output parameters that are initially loaded from the ROM 212, flash 206, or from a table 304 within the non-volatile memory 210 during bootup of the device 102.

The processor 202 loads default programming into the operating memory 204 but a normal mode set of values are specified at location 324 of a table 316 in the operating memory 204 once a programming session with an external programmer is complete. The programming specifies the various mode parameter values that are stored at a location 326. Upon an external device programming the IMD 102 to enter the MRI mode, the processor 202 stores a table 312 to the operating memory 204 where the table 312 has a location 318 that stores the value indicating the MRI mode state, a location 320 that provides the MRI mode values, and a location 322 that provides the MRI mode parameter values. The processor 202 copies the contents of the table 312 to the table 302 within the non-volatile memory 210 so that this MRI mode information of the table 302 may be copied back to the operating memory 204 once a device reset occurs while MRI mode state is active.

The MRI mode values stored at locations 308 and 320 specify the mode of stimulation, including which channels corresponding to a particular region of the heart are to provide stimulation, that sensing of intrinsic beats is off and therefore that the stimulation is to be asynchronous to the intrinsic beats. The MRI mode parameter values stored at locations 310 and 322 specify values for variables including the pulse amplitude for each channel that is active, the pulse width for each channel that is active, the pulse interval for each channel that is active, and so forth.

While the normal mode values are not being stored to the non-volatile memory 210 in this example, in other examples that may be done as well. In such a case, the IMD 102 can recover to the normal mode when a device reset occurs during normal mode stimulation when the MRI mode state is set to inactive. It may be desirable to only store the MRI mode or other special mode parameters to the non-volatile memory 210 in some embodiments in order to minimize the number of read/writes from the non-volatile memory 210 to thereby preserve the operating life of the non-volatile memory 210.

Figure 4A:
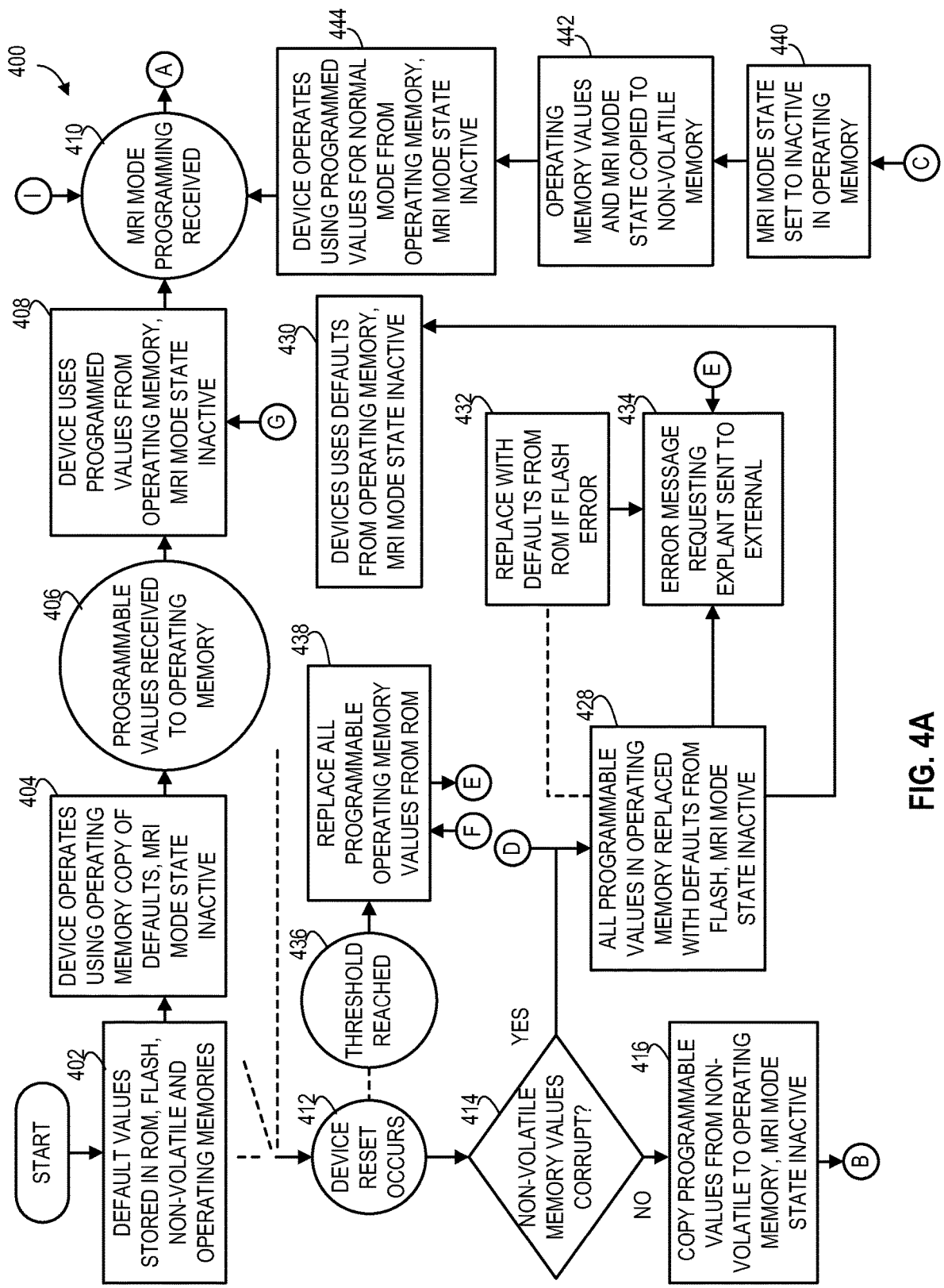
FIGS. 4A and 4B show an example of logical operations performed by the processor when an MRI mode of operation is inactive.
Figure 4B:
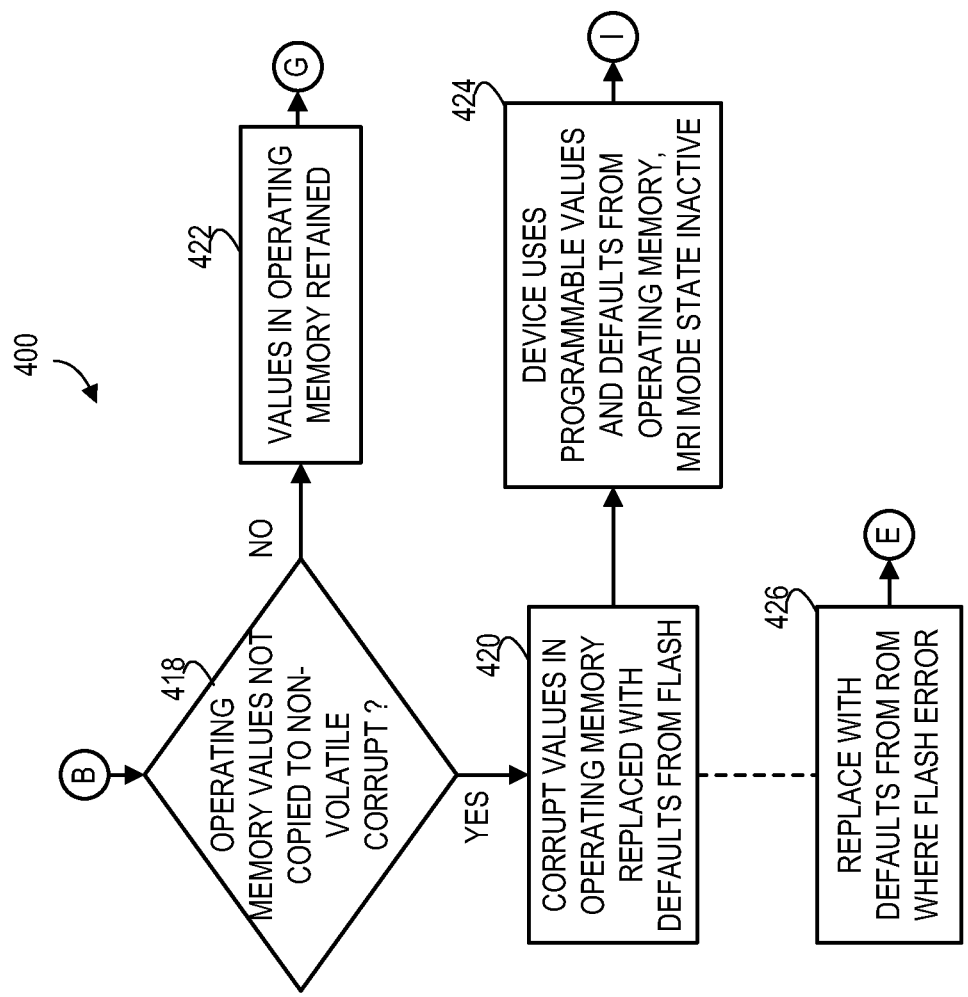
Figure 5A:
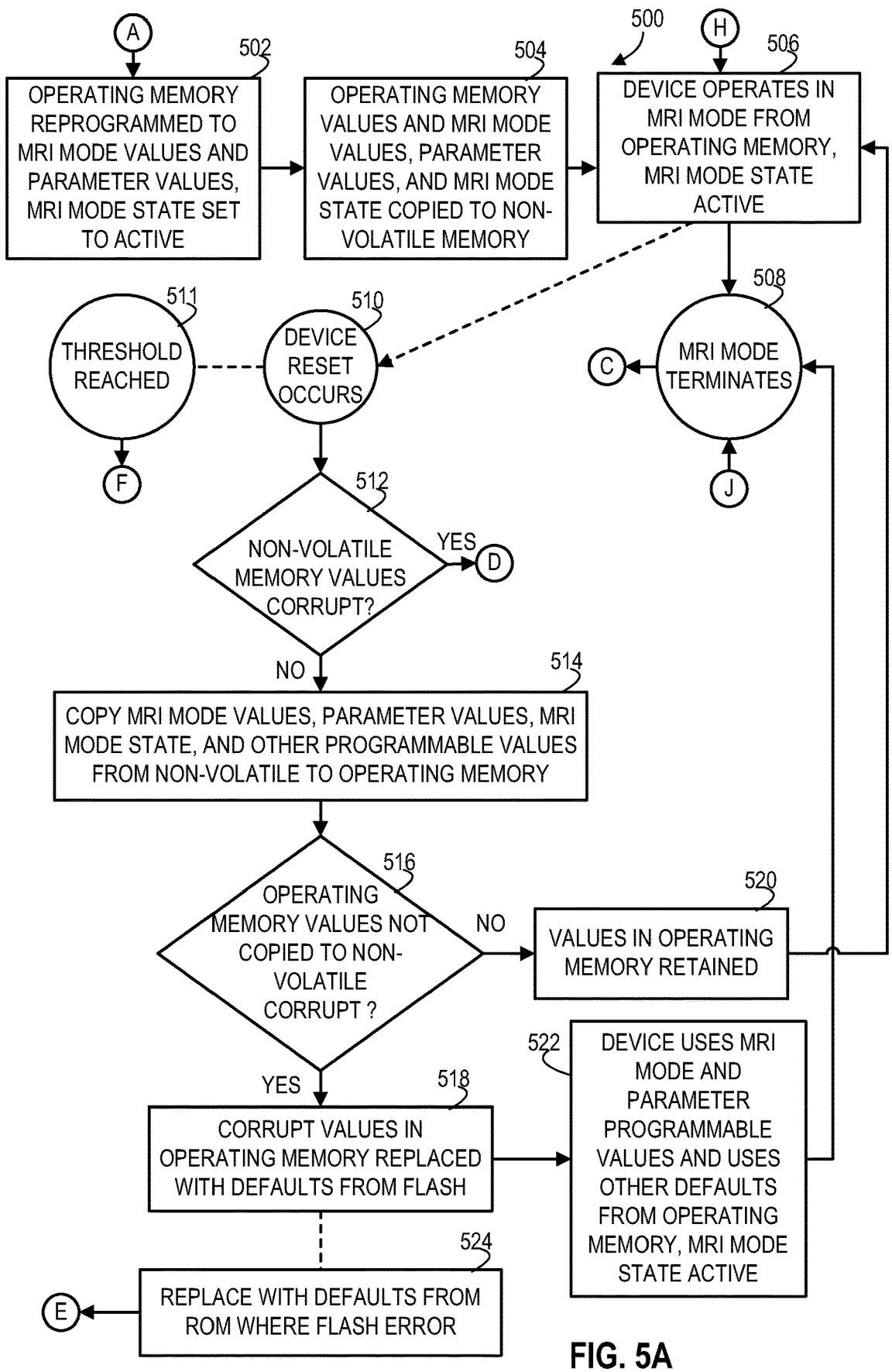
FIG. 5A shows an example of logical operations performed by the processor when the MRI mode of operation is active.
Figure 5B:
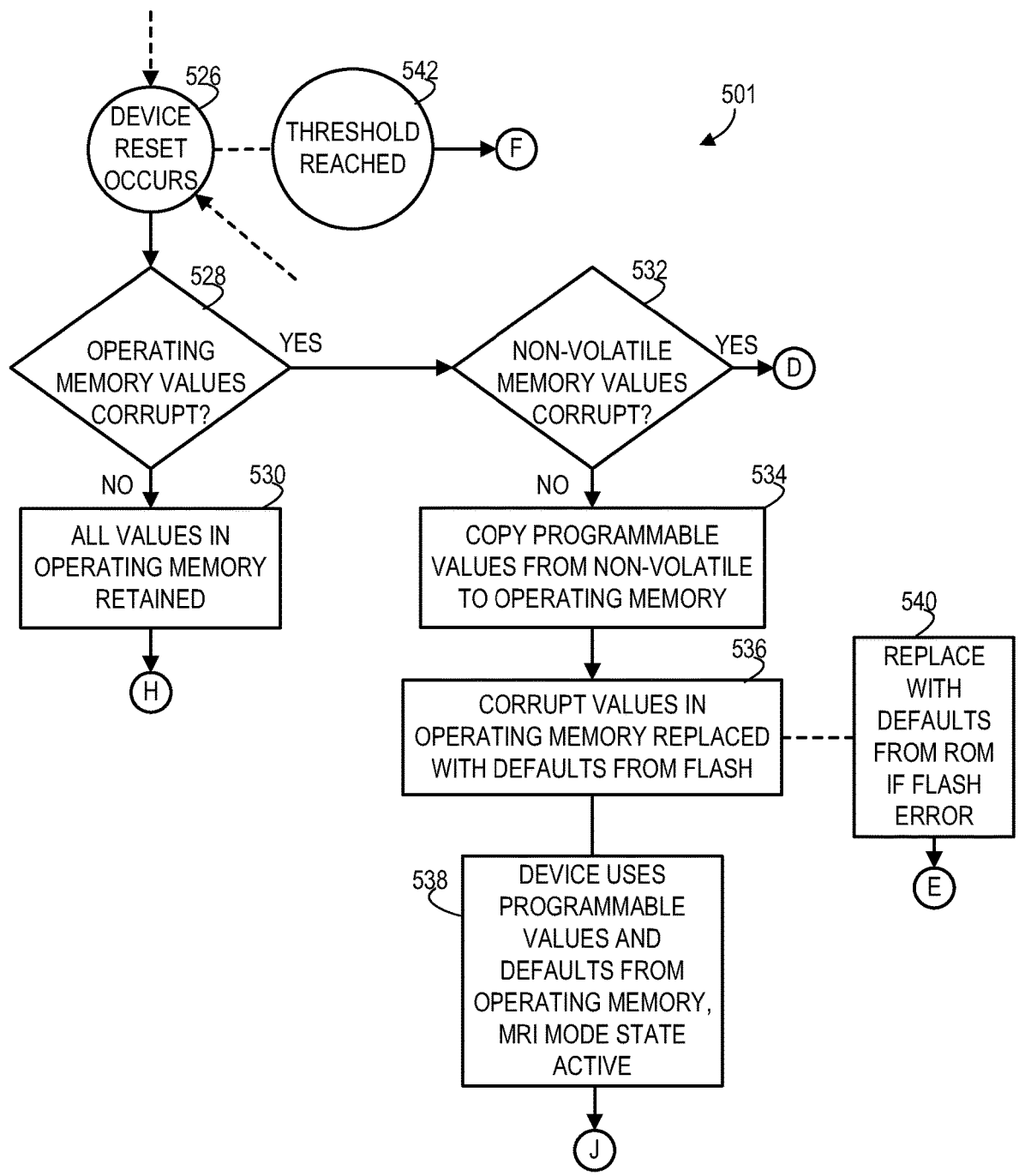
FIG. 5B shows an alternative set of logical operations performed by the processor when the MRI mode of operation is active.

FIGS. 4A, 4B, and 5A show sets of logical operations that may be performed by the processor 202. Specifically, FIGS. 4A and 4B show a set of operations 400 performed while the MRI mode state is inactive while FIG. 5A shows a set of operations 500 performed while the MRI mode state is active. FIG. 5B shows an alternate portion of the operations 501 performed while the MRI mode state is active.

The set of operations 400 begin at an operation 402 where default values are stored in the various memory components which in this example include the ROM 212, flash 206, non-volatile memory 210, and operating memory 204 to prepare the IMD 102 to function. As stated above, the particular configuration of memory components are provided as an example and other configurations are also applicable. The IMD 102 then operates by the processor 202 using the default values from the operating memory 204 including the MRI mode state being inactive at operation 404 until other programmable values that define the normal mode of stimulation are received via telemetry and stored into the operation memory 204 at the event 406. The IMD 102 then begins the normal mode of operation by the processor 202 accessing the normal mode values from the operating memory 204 including reading the MRI mode state value of inactive at an operation 408.

At any time during the normal mode of operation, a device reset may occur at event 412. The dashed lines leading to the event 412 illustrate that the device reset event 412 may occur during any of the preceding or subsequent operations. The device reset may be triggered by ambient conditions other than the IMD 102 being in proximity to an MRI machine and in such cases the IMD 102 is operating in the normal mode rather than the MRI mode when the device reset occurs. If the number of device resets for a given period of time has not reached a threshold, then immediately after the device reset the processor 202 detects whether the non-volatile memory 210 is corrupt at a query 414. This may be done by performing a cyclic redundancy check on the contents of the non-volatile memory 210.

When the non-volatile memory 210 is not corrupted, the processor 202 then copies programmable values stored in the non-volatile memory 210 to the operating memory 204 including the value indicating that the MRI mode state is inactive at an operation 416. In one example, the normal mode values that were programmed to the operating memory at the event 406 have not been copied to the non-volatile memory 210 as shown in FIG. 3. Therefore, the programmable values from the non-volatile memory 210 in this example are the values for the more basic functionality of the IMD 102. For the values in the operating memory 204 that establish the normal mode and that have not been copied to the non-volatile memory 210, the processor 202 detects whether those values in the operating memory 204 are corrupt at a query 418.

Where the values in the operating memory 204 that define the normal mode are not corrupt, those values are retained in the operating memory 204 at an operation 422. At this point, the operating memory 204 has all values necessary for returning to the normal mode of stimulation at the operation 408.

Where the values in the operating memory 204 that define the normal mode are corrupt, the processor 202 then replaces those values with default values. In this example, the processor 202 first attempts to copy those values from the flash memory 206 at operation 420. Where that is successful, the IMD 102 then proceeds to operate in the default mode using the programmable values from the non-volatile memory 210 and the default values for the mode from the flash 206 that are now in the operating memory 204 at an operation 424. The processor reads that the MRI mode state value is inactive, and the device 102 proceeds in this default mode of stimulation until receiving new programming at a later time.

If the attempt to copy the default values from the flash memory 206 fails due to a flash error, the processor 202 then resorts to copying default values from the ROM 212 at an operation 426 in order to place the IMD 102 into a bootup mode. This ensures the IMD 102 has the ability to communicate via the telemetry circuit 208. At the next communication session, the processor 202 then sends an error message to the external programmer that requests that the IMD 102 be explanted due to the corruption of the flash memory 206 at an operation 434.

For the alternative where the normal mode values are stored in the non-volatile memory 210 and those values are not corrupt at the query 414, then those values may also be copied to the operating memory 204 at the operation 416. The normal mode of stimulation may then proceed at the operation 408 where the processor reads that the MRI mode state is inactive.

Returning to the query 414, if the processor 202 finds the values in the non-volatile memory are corrupt, then all values in the operating memory 204 are replaced by the processor 202 copying default values from the flash memory 206 including the MRI mode state being inactive at an operation 428. The IMD 102 then proceeds to operate in the default mode using the default values for the mode from the flash 206 that are now in the operating memory 204 at an operation 430, including the processor reading that the MRI mode state value is inactive. The device 102 proceeds in this default mode until receiving new programming at a later time.

If the attempt to copy the default values from the flash memory 206 fails due to a flash error, the processor 202 then resorts to copying default values from the ROM 212 at an operation 432 in order to place the IMD 102 into the bootup mode. At the next communication session, the processor 202 then sends an error message to the external programmer that requests that the IMD 102 be explanted due to the corruption of the flash memory 206 at the operation 434.

Returning to the device reset at the event 412, if the threshold number of device resets has been reached for a given period of time as determined by the processor 202 at the event 436, then the processor 202 replaces all of the programmable values in the operating memory 204 from the ROM 212 at an operation 438. This places the IMD 102 into the bootup mode. At the next communication session, the processor 202 then sends an error message to the external programmer that requests that the IMD 102 be explanted due to the large number of device resets at the operation 434.

Thus far, the operation of the IMD 102 has been described for the MRI mode state being inactive in the operating memory 204 and in the non-volatile memory 210. However, while the IMD 102 is operating in the normal mode at operation 408 or the default mode at operation 424, a programming session may occur to place the IMD 102 into the MRI mode at an event 410. This event 410 transitions the IMD 102 to the set of operations 500 of FIG. 5A.

The processor 202 reprograms the operating memory 204 with MRI mode values and parameter values for the MRI mode received from the external programmer at an operation 502. The processor 202 also sets the MRI mode state value in the operating memory 204 to indicate that the MRI mode is active. The processor 202 also copies the values from the operating memory 204 including the MRI mode values, mode parameter values, and MRI mode state to the non-volatile memory 210 at an operation 504.

The processor 202 utilizes these values in the operating memory 204 including reading that the MRI mode state value is active to begin implementing the MRI mode of stimulation at an operation 506. The MRI mode continues until a termination occurs at an event 508. The termination may result from various events. For example, a programming session may be established during the MRI mode where the external programmer instructs the processor 202 to exit the MRI mode. As another example, the MRI mode may have a timeout period that once reached triggers the processor 202 to terminate the MRI mode. The event 508 transitions the IMD 102 back to the set of operations 400.

However, at any time while the MRI mode is active, a device reset may be triggered at an event 510. For instance, the device reset may be triggered by ambient conditions resulting from being in proximity to an MRI machine. If the number of device resets for a given period of time has not reached a threshold, then immediately after the device reset the processor 202 detects whether the non-volatile memory 210 is corrupt at a query 512. As previously stated, this may be done by performing a cyclic redundancy check on the contents of the non-volatile memory 210.

When the non-volatile memory 210 is not corrupted, the processor 202 then copies the programmable values stored in the non-volatile memory 210 to the operating memory 204 including the MRI mode values, the mode parameter values, and the value indicating that the MRI mode state is active. The programmable values from the non-volatile memory 210 also include the values for the more basic functionality of the IMD 102. For any other values in the operating memory 204 that that were not copied to the non-volatile memory 210, the processor 202 detects whether those values in the operating memory 204 are corrupt at a query 516.

Where these additional values in the operating memory 204 are not corrupt, those values are retained in the operating memory 204 at an operation 520. At this point, the operating memory 204 has all values necessary for returning to the MRI mode of stimulation where the processor 202 reads that the MRI mode state value is active at the operation 506. Thus, the IMD 102 recovers from the device reset by immediately continuing the MRI mode of therapy based on operating memory 204 values without prior post reset implementation of any other mode.

Where these additional values in the operating memory 204 are corrupt, the processor 202 then replaces those values with default values. In this example, the processor 202 first attempts to copy those values from the flash memory 206 at operation 518. Where that is successful, the IMD 102 then proceeds to operate in the MRI mode where the processor 202 reads that the MRI mode state value is active at an operation 522. The processor 202 uses the programmable MRI mode values from the non-volatile memory 210 and any other values needed are default values for the mode from the flash 206 that are now in the operating memory 204. The device 102 proceeds in the MRI mode until a termination event such as receiving new programming at a later time or reaching an MRI mode timeout. Thus, in this scenario the IMD 102 also recovers from the device reset by immediately continuing the MRI mode of therapy based on operating memory 204 values without prior post reset implementation of any other mode.

If the attempt to copy the default values from the flash memory 206 fails due to a flash error, the processor 202 then resorts to copying default values from the ROM 212 at an operation 524 in order to place the IMD 102 into the bootup mode. At the next communication session, the processor 202 then sends an error message to the external programmer that requests that the IMD 102 be explanted due to the corruption of the flash memory 206 at an operation 434.

Returning to the query 512, if the processor 202 finds the values in the non-volatile memory are corrupt, then the IMD 102 transitions back to the set of operations 400. At operation 428 all values in the operating memory 204 are replaced by the processor 202 copying default values from the flash memory 206 including the MRI mode state being inactive at an operation 428. The IMD 102 then proceeds to operate in the default mode using the default values for the mode from the flash 206 that are now in the operating memory 204 at an operation 430. The device 102 proceeds in this default mode until receiving new programming at a later time.

Returning to the device reset at the event 510, if the threshold number of device resets has been reached for a given period of time as determined by the processor 202 at the event 511, then the IMD 102 transitions back to the set of operations 400. The processor 202 replaces all of the programmable values in the operating memory 204 from the ROM 212 at the operation 438.

Returning to the termination of the MRI mode at the event 508, the IMD 102 transitions to an operation 440 where the processor 202 sets the MRI mode state value to inactive in the operating memory 204. The processor 202 also copies the values of the operating memory 204 including the MRI mode state to the non-volatile memory 210 at an operation 442. The processor 202 then uses the programmed values for the normal mode that are present in the operating memory 204 to begin implementing the normal mode of stimulation until receiving further programming at an operation 444. In doing so, the processor 202 reads that the MRI mode state value is inactive.

The IMD 102 may instead implement the alternate logical operations 501 of FIG. 5B for the portion of the operations 500 that occur after a device reset. At an event 526, it is first determined whether the number of device resets for a given period of time has not reached a threshold. If so, at a threshold event 542, the IMD 102 then transitions back to the set of operations 400 and specifically to operation 438. If the threshold has not been reached, then immediately after the device reset the processor 202 detects whether the values in the operating memory 204 are corrupt at a query 528. This may be done by performing a cyclic redundancy check on the contents of the operating memory 204.

When the operating memory 204 is not corrupted, the processor 202 then retains all values in the operating memory including the MRI mode values, mode parameter values, and MRI mode state at an operation 530. At this point, the operating memory 204 already has all values necessary for returning to the MRI mode of stimulation at the operation 506 of FIG. 5A.

When the operating memory 204 is corrupted, the processor 202 then detects whether the non-volatile memory 210 is corrupted at query 532. If so, then the IMD transitions to the set of operations 400 where at operation 428 all values in the operating memory 204 are replaced by the processor 202 copying default values from the flash memory 206 including the MRI mode state being inactive at an operation 428. The IMD 102 then proceeds to operate in the default mode using the default values for the mode from the flash 206 that are now in the operating memory 204 at an operation 430. The device 102 proceeds in this default mode until receiving new programming at a later time.

When the non-volatile memory 210 is not corrupted, the processor 202 copies the programmable values stored in the non-volatile memory 210 to the operating memory 204 at an operation 534. These values include the MRI mode values, the mode parameter values, and the value indicating that the MRI mode state is active. The programmable values from the non-volatile memory 210 also include the values for the more basic functionality of the IMD 102. For any other values in the operating memory 204 that were not copied to the non-volatile memory 210, the processor 202 then replaces those values with default values. In this example, the processor 202 first attempts to copy those values from the flash memory 206 at operation 536. Where that is successful, the IMD 102 then proceeds to operate in the MRI mode where the processor 202 reads that the MRI mode state value is active at operation 538. The processor 202 uses the programmable MRI mode values from the non-volatile memory 210 and any other values needed are default values for the mode from the flash 206 that are now in the operating memory 204. The device 102 proceeds in the MRI mode until an event 508 occurs to terminate the mode, such as receiving new programming at a later time or reaching an MRI mode timeout.

If the attempt to copy the default values from the flash memory 206 fails due to a flash error, the processor 202 then resorts to copying default values from the ROM 212 at an operation 540 in order to place the IMD 102 into the bootup mode. This transitions the IMD 102 back to the set of operations 400 where the MRI mode state is inactive. At the next communication session, the processor 202 then sends an error message to the external programmer that requests that the IMD 102 be explanted due to the corruption of the flash memory 206 at the operation 434.

While specific examples of the logical operations performed by the processor 202 have been described above in relation to FIGS. 4A-5B, these examples are not intended to be limiting. Many variations to these logical operations are possible and fall within the scope of this disclosure. For instance, rather than entering a bootup mode from the ROM 212, the ROM may instead provide the same default parameters that are provided by the flash memory 206. Relying on the defaults from the ROM 212 may or may not trigger the explant request, and so forth.

While embodiments have been particularly shown and described, it will be understood by those skilled in the art that various other changes in the form and details may be made therein without departing from the spirit and scope of the invention.

What is claimed is:

1. A method of operating an implantable medical device during a condition that may trigger a device reset, comprising:
    receiving mode programming at the device that defines a special mode of operation to utilize during the condition and receiving parameter programming that specifies therapy parameters to utilize for the special mode of operation;
    storing the mode programming and the parameter programming in a non-volatile memory;
    storing a value in the non-volatile memory indicating whether the special mode is active;
    upon experiencing a device reset, reading the value that indicates whether the special mode is active;
    loading the mode programming and parameter programming from the non-volatile memory to an operating memory; and
    in response to reading the value when the value indicates that the special mode is active, implementing the special mode defined by the mode programming from the operating memory.

2. The method of claim 1, wherein the device reset terminates a mode of operation occurring prior to the device reset, the method further comprising implementing the special mode defined by the mode programming from the operating memory prior to implementing any other stimulation mode once the device reset has occurred.

3. The method of claim 1, wherein the implantable medical device includes a field programmable processor and wherein the field programmable processor implements the special mode from the operating memory.

4. The method of claim 1, wherein the operating memory is volatile.

5. The method of claim 1, further comprising implementing the special mode from the operating memory prior to the device reset.

6. The method of claim 5, further comprising detecting after the reset and prior to loading the mode programming whether the operating memory contains valid programming of a mode and when the operating memory contains the valid programming of the mode, not loading mode programming and parameter programming from the non-volatile memory.

7. The method of claim 1, wherein the condition is an MM scan and wherein the special mode is an MM mode.

8. An implantable medical system that operates during a condition that may trigger a device reset, comprising:
    an implantable medical lead having a proximal contact and a distal electrode; and
    an implantable medical device, comprising:
        a pulse generator;
        an electrical connector that is electrically coupled to the pulse generator, the proximal contact being electrically coupled to the electrical connector;
        an operating memory;
        a non-volatile memory;
        a telemetry communication circuit;
        a processing device in communication with the pulse generator, the operating memory, the non-volatile memory, and the telemetry communication circuit, the processing device being configured to:
            receive from the telemetry communication circuit mode programming that defines a special mode of electrical stimulation to utilize during the condition and receive parameter programming that specifies stimulation parameters to utilize for the special mode of electrical stimulation;

store the mode programming and the parameter programming in the non-volatile memory;

store a value in the non-volatile memory indicating whether the special mode is active;

upon experiencing a device reset, read the value that indicates whether the special mode is active;

load the mode programming and parameter programming from the non-volatile memory to the operating memory;

and in response to reading the value when the value indicates that the special mode is active, implement the special mode defined by the mode programming from the operating memory by controlling operation of the pulse generator.

9. The implantable medical system of claim 8, wherein the device reset terminates a stimulation mode occurring prior to the device reset, and wherein the processing device is further configured to implement the special mode defined by the mode programming from the operating memory prior to implementing any other stimulation mode once the device reset has occurred.

10. The implantable medical system of claim 8, wherein the processing device comprises a field programmable processor and wherein the field programmable processor implements the special mode from the operating memory.

11. The implantable medical system of claim 8, wherein the operating memory is volatile.

12. The implantable medical system of claim 8, wherein the processing device implements the special mode from the operating memory prior to the device reset.

13. The implantable medical system of claim 12, wherein the processing device is further configured to detect after the device reset and prior to loading the mode programming whether the operating memory contains valid programming of a mode and when the operating memory contains the valid programming of the mode, not loading mode programming and parameter programming from the non-volatile memory.

* * * * *